(12) United States Patent
Fonquerna Pou et al.

(10) Patent No.: US 7,560,471 B2
(45) Date of Patent: Jul. 14, 2009

(54) INDOLYLPIPERIDINE DERIVATIVES AS POTENT ANTIHISTAMINIC AND ANTIALLERGIC AGENTS

(75) Inventors: Silvia Fonquerna Pou, Barcelona (ES); Luis Miguel Pages Santacana, Barcelona (ES)

(73) Assignee: Laboratorios Almirall S.A., Barcelona (ES)

( * ) Notice: Subject to any disclaimer, the term of this patent is extended or adjusted under 35 U.S.C. 154(b) by 613 days.

(21) Appl. No.: 10/515,407

(22) PCT Filed: May 19, 2003

(86) PCT No.: PCT/EP03/05222

§ 371 (c)(1),
(2), (4) Date: Jul. 11, 2005

(87) PCT Pub. No.: WO03/099807

PCT Pub. Date: Dec. 4, 2003

(65) Prior Publication Data

US 2006/0094879 A1    May 4, 2006

(30) Foreign Application Priority Data

May 29, 2002    (ES)    ................. 200201226

(51) Int. Cl.
*A61K 31/454*    (2006.01)
*C07D 403/02*    (2006.01)
(52) U.S. Cl. ...................... 514/323; 546/201
(58) Field of Classification Search ................. 514/323; 546/201
See application file for complete search history.

(56) References Cited

U.S. PATENT DOCUMENTS

| 5,650,416 | A | 7/1997 | Carr et al. | |
| 6,683,096 | B2 * | 1/2004 | Pages Santacana et al. | 514/323 |
| 7,189,741 | B2 * | 3/2007 | Fonquerna Pou et al. | 514/323 |

FOREIGN PATENT DOCUMENTS

| EP | 0 224919 A2 | 6/1987 |
| EP | 0 324 431 A1 | 7/1989 |
| EP | 0 378 255 A2 | 7/1990 |
| EP | 648 759 A1 | 4/1995 |
| WO | WO95/01350 A1 | 1/1995 |
| WO | WO00/75130 A1 | 12/2000 |
| WO | WO02/14317 A2 | 2/2002 |
| WO | WO02/20013 A2 | 3/2002 |
| WO | WO02/36589 A1 | 5/2002 |

OTHER PUBLICATIONS

Santacana et al. "Indolylpiperidine . . . " CA 134:42067 (2000).*
Fonquerna et al. "Preparation of indolypiperidines . . . " CA 1136:369609 (2002).*

* cited by examiner

*Primary Examiner*—Celia Chang
(74) *Attorney, Agent, or Firm*—Finnegan, Henderson, Farabow, Garret & Dunner, LLP

(57) ABSTRACT

This invention is directed to new potent and selective antagonists of $H_1$ histamine receptors having the general formula I

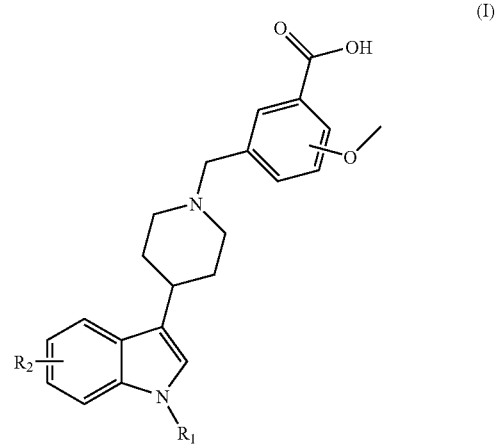

to processes for their preparation; to pharmaceutical compositions comprising them; and to their use in therapy as antiallergic agents.

9 Claims, No Drawings

INDOLYLPIPERIDINE DERIVATIVES AS POTENT ANTIHISTAMINIC AND ANTIALLERGIC AGENTS

This application is a national stage filing under 35 U.S.C. § 371 of International Application No. PCT/EP03/05222, filed on May 19, 2003. This application claims the benefit of priority under 35 U.S.C. § 119 to Spanish Patent Application No. P200201226 filed on May 29, 2002.

The present invention relates to a novel class of indolylpiperidine derivatives and pharmaceutically acceptable salts thereof. These compounds are selective antagonists of $H_1$ histamine receptors and have more potent antihistaminic activity in vivo. They are thus particularly useful for the treatment of bronchial asthma, allergic rhinitis, conjunctivitis, dermatitis, urticaria and other allergic diseases.

WO 0075130 discloses selective antagonists of $H_1$ histamine receptors having an indolylpiperidine core. It has now been found that a specific group of compounds falling under the general formula in WO 0075130, but which are not explicitly disclosed there, show an increased selectivity on $H_1$ histamine receptors with respect to 5HT-2 serotonin receptors and, at the same time, are significantly more potent antihistaminic compounds in vivo.

Thus, the present invention provides a selection of indolylpiperidine compounds having more potent and selective antiallergic effects. This allows to achieve a clinical improvement of the symptoms of allergic diseases with lower doses, preventing almost completely the occurrence of sedative and cardiovascular side effects, which are characteristic of most commercial antihistamines.

Further objectives of the present invention are to provide a method for preparing said compounds; pharmaceutical compositions comprising an effective amount of said compounds; the use of the compounds in the manufacture of a medicament for the treatment of diseases susceptible of being improved by antagonism of $H_1$ histamine receptors, such as allergic diseases; and methods of treatment of diseases susceptible to amelioration by antagonism of $H_1$ histamine receptors, such as allergic diseases, comprising the administration of the compounds of the invention to a subject in need of treatment.

With respect to the compounds explicitly disclosed in WO 0075130 the advantageous effects of the compounds of the invention are due to their distinguishing structural features. More specifically, the compounds of the invention are characterised by the general structure of formula (I)

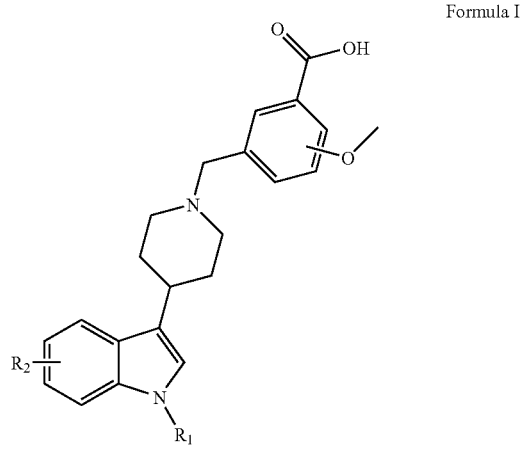

Formula I wherein:

$R_1$ represents an alkyl, alkenyl, alkoxyalkyl or cycloalkylalkyl group;

$R_2$ represents a hydrogen or halogen atom;

the methoxy group substituting the benzoic acid is in position ortho with respect to the carboxy group.

and pharmaceutically acceptable salts thereof.

As used herein, an alkyl group or moiety is a linear straight or branched group or moiety. Typically it is a $C_1$-$C_{10}$ group or moiety, preferably a $C_1$-$C_6$ group or moiety. Examples include methyl, ethyl, i-propyl, n-propyl, n-butyl, sec-butyl, t-butyl, n-pentyl, 1-methylbutyl, 1-ethylpropyl, 1,2-dimethylpropyl, n-hexyl or 1-ethylbutyl. Most preferably it is a straight $C_1$-$C_4$ group or moiety.

As used herein, an alkenyl group or moiety is a linear straight or branched group or moiety. Typically it is a $C_2$-$C_{10}$ group or moiety, preferably a $C_2$-$C_6$ group or moiety, most preferably it is a straight $C_1$-$C_4$ group or moiety. Examples include allyl or 2-propenyl.

As used herein, the alkyl chains present in the alkoxyalkyl and cycloalkylalkyl groups are typically linear straight or branched alkyl chains containing from 1 to 6 carbon atoms, most preferably from 1 to 4 carbon atoms. In the alkoxyalkyl groups they may be the same or different.

As used herein, a cycloalkyl group is typically unsubstituted and has from 3 to 6 carbon atoms. Examples include cyclopropyl, cyclobutyl, cyclopentyl and cyclohexyl. It is preferably cyclopropyl, cyclopentyl or cyclohexyl.

As used herein a halogen atom is one of chlorine, fluorine, bromine or iodine. Preferably chlorine or fluorine.

Compounds of formula (I) containing one or more chiral centre may be used in enantiomerically or diastereoisomerically pure form, or in the form of a mixture of isomers.

As used herein, a pharmaceutically acceptable salt is a salt with a pharmaceutically acceptable acid or base. Pharmaceutically acceptable acids include both inorganic acids, for example hydrochloric, sulphuric, phosphoric, diphosphoric, hydrobromic and nitric acid and organic acids, for example citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, aralkyl amines and heterocyclic amines.

Preferred compounds of the invention are those wherein the methoxy group substituting the benzoic acid is both in position ortho with respect to the carboxy group and in position para with respect to the carbon atom which is bound to the indolylpiperidine moiety of the molecule as shown in formula Ia.

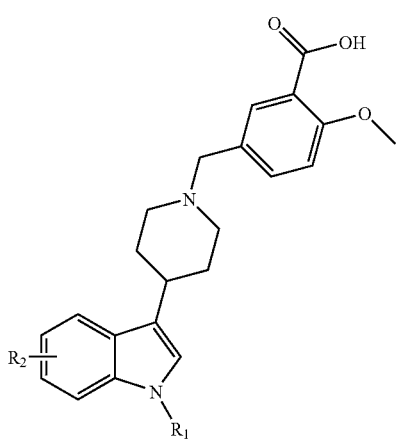

Formula Ia

Preferred compounds of the invention are those wherein $R_1$ is selected from ethyl, n-propyl, n-butyl, methoxymethyl, methoxyethyl, ethoxyethyl, cyclopropylmethyl, cyclopentylmethyl, cyclohexylmethyl, cyclopropylethyl, allyl, 2-propenyl, 2-propoxyethyl and 3-methoxypropyl. Most preferably $R_1$ is methoxyethyl, ethoxyethyl, butyl, cyclopropylmethyl or allyl.

Also preferred are compounds wherein $R_2$ is hydrogen, fluorine or chlorine. Most preferably, $R_2$ is hydrogen or fluorine.

Particular individual compounds of the invention include:
1. 5-{4-[1-(2-ethoxyethyl)-1H-indol-3-yl]piperidin-1-ylmethyl}-2-methoxybenzoic acid
2. 2-methoxy-5-{4-[1-(2-methoxyethyl)-1H-indol-3-yl]piperidin-1-ylmethyl}-benzoic acid
3. 5-[4-(1-butyl-1H-indol-3-yl)-piperidin-1-ylmethyl]-2-methoxybenzoic acid
4. 5-{4-[1-(2-ethoxyethyl)-6-fluoro-1H-indol-3-yl]piperidin-1-ylmethyl}-2-methoxybenzoic acid
5. 5-{4-[6-fluoro-1-(2-methoxyethyl)-1H-indol-3-yl]piperidin-1-ylmethyl}-2-methoxybenzoic acid
6. 5-[4-(1-butyl-6-fluoro-1H-indol-3-yl)-piperidin-1-ylmethyl]-2-methoxybenzoic acid
7. 5-[4-(5-bromo-1-propyl-1H-indol-3-yl)-piperidin-1-ylmethyl]-2-methoxybenzoic acid
8. 3-[4-(5-chloro-1-ethyl-1H-indol-3-yl)-piperidin-1-ylmethyl]-2-methoxybenzoic acid
9. 3-[4-(1-cyclopropylmethyl-5-fluoro-1H-indol-3-yl)-piperidin-1-ylmethyl]-2-methoxybenzoic acid
10. 5-[4-(5-chloro-1-cyclohexylmethyl-1H-indol-3-yl)-piperidin-1-ylmethyl]-2-methoxybenzoic acid
11. 2-methoxy-5-{4-[1-(2-propoxyethyl)-1H-indol-3-yl]-piperidin-1-ylmethyl}-benzoic acid
12. 3-{4-[5-bromo-1-(3-methoxypropyl)-1H-indol-3-yl]-piperidin-1-ylmethyl}-2-methoxybenzoic acid
13. 3-[4-(1-allyl-1H-indol-3-yl)-piperidin-1-ylmethyl]-2-methoxybenzoic acid
14. 3-[4-(1-allyl-6-fluoro-1H-indol-3-yl)-piperidin-1-ylmethyl]-2-methoxybenzoic acid
15. 5-{4-[5-chloro-1-(2-propenyl)-1H-indol-3-yl]-piperidin-1-ylmethyl}-2-methoxybenzoic acid
16. 5-[4-(1-cyclopentylmethyl-6-fluoro-1H-indol-3-yl)-piperidin-1-ylmethyl]-2-methoxybenzoic acid
17. 3-{4-[6-fluoro-1-methoxymethyl-1H-indol-3-yl]-piperidin-1-ylmethyl}-2-methoxybenzoic acid
18. 3-{4-[1-cyclopropylethyl-1H-indol-3-yl]-piperidin-1-ylmethyl}-2-methoxybenzoic acid
19. 3-{4-[5-chloro-1-(2-methoxyethyl)-1H-indol-3-yl]-piperidin-1-ylmethyl}-2-methoxybenzoic acid
20. 3-{4-[1-(2-ethoxyethyl)-5-fluoro-1H-indol-3-yl]-piperidin-1-ylmethyl}-2-methoxybenzoic acid.

In accordance with another embodiment, the present invention provides a method for preparing the indolylpiperidine compounds represented by formula I. These compounds are prepared according to Scheme 1 starting from an intermediate of general formula VIII wherein $R_1$ and $R_2$ are as defined above and $R_3$ is an alkyl group.

Scheme 1

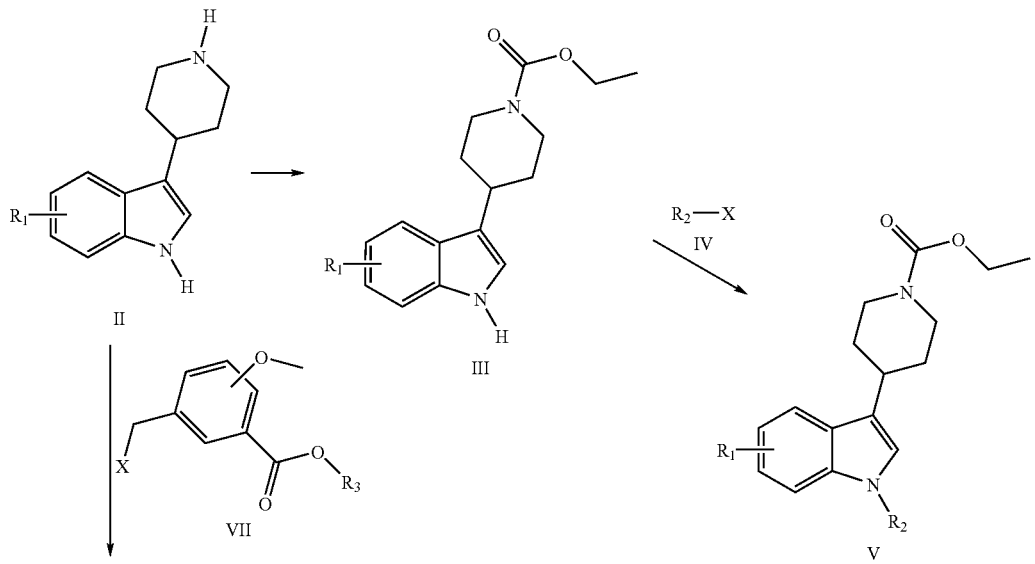

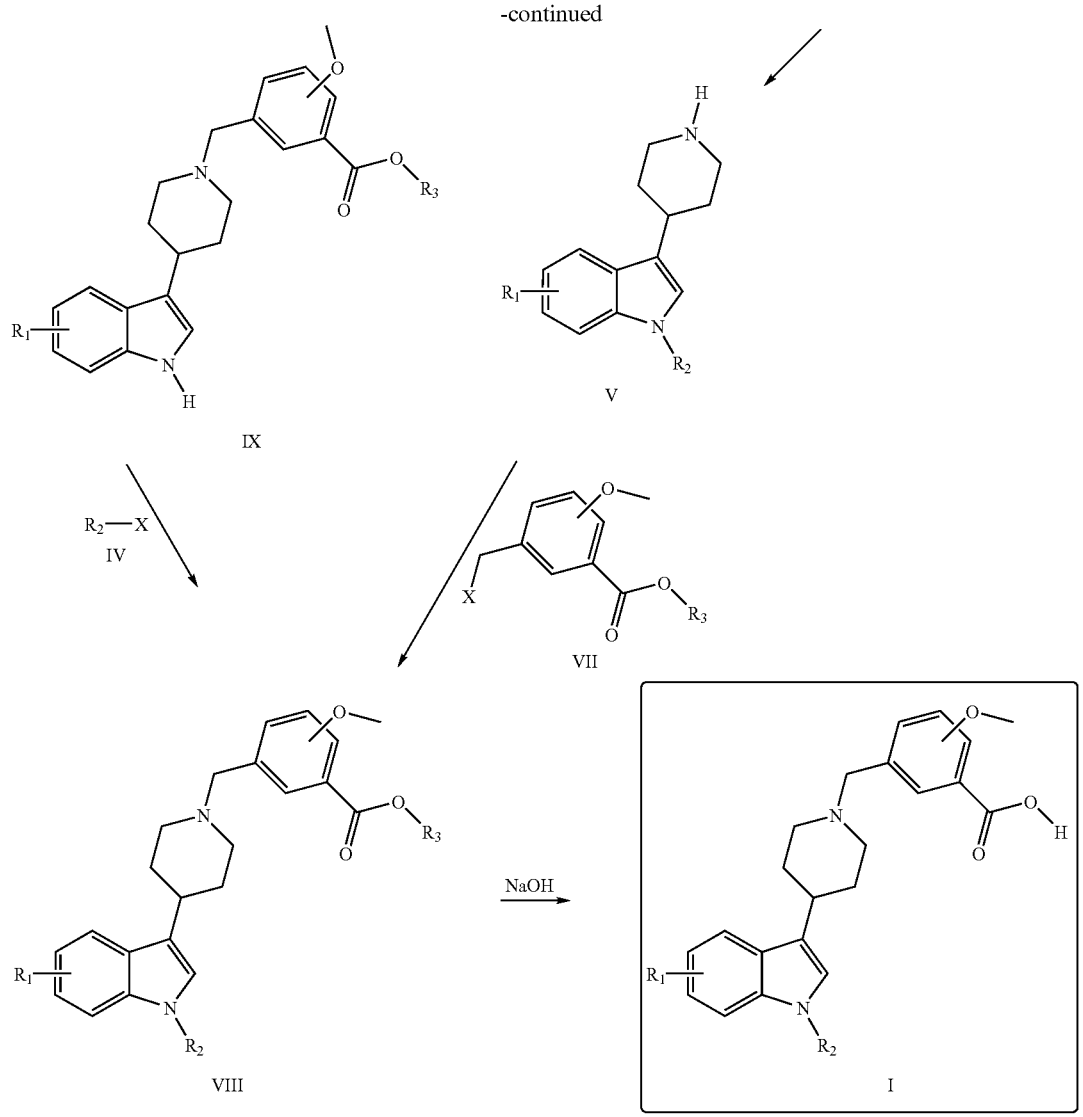

The intermediate of formula VIII is treated with sodium or potassium hydroxide in a solvent such as methanol, ethanol or tetrahydrofuran at a temperature between 25° C. and 60° C.

Further treatment with an inorganic acid such as hydrochloric acid provides the corresponding indolylpiperidine derivatives of general formula I wherein $R_1$ and $R_2$ are as defined above.

The compound of formula VIII can be prepared following two different pathways (see Scheme 1).

According to the first pathway, a compound of general structure II wherein $R_1$ is as defined above, is treated with ethyl chloroformate in the presence of a base such as triethylamine or pyridine at a temperature between 0° C. and room temperature to give a compound of formula III wherein $R_1$ is as defined above.

The alkylation of compound III with a reactive intermediate of formula IV wherein $R_2$ is as defined above and X is a leaving group, such as a chlorine or a bromine atom or a methane sulphonate, p-toluensulphonate or a benzenesulphonate group, gives a compound of general formula V, wherein $R_1$ and $R_2$ are as defined above. This reaction is preferably carried out in an inert solvent such as dimethylformamide, tetrahydrofuran or ethyl ether at a temperature between 0° C. and 80° C. in the presence of an inorganic base such as sodium hydride or sodium amide.

Compound V is deprotected by boiling it in the presence of an excess of sodium or potassium hydroxide in an alcoholic solvent such as ethanol, isopropanol or n-butanol at a temperature between 80° C. and 180° C. This leads to a compound of general formula VI, wherein $R_1$ and $R_2$ are as defined above.

Further alkylation of compound VI with a reactive intermediate of formula VII wherein $R_3$ is as defined above and X is a leaving group, such as a chlorine or a bromine atom or a methane sulphonate, p-toluene sulphonate or a benzene sulphonate group, gives a compound of formula VIII wherein $R_1$, $R_2$ and $R_3$ are as defined above. This reaction is preferably carried out in an organic solvent such as toluene, dicloromethane, dioxane or methyl isobutylketone at a temperature between 25° C. and 140° C. in the presence of a base such as an alkali metal carbonate or bicarbonate, triethylamine or diisopropilethylamine.

Alternatively, the novel indolylpiperidine derivatives of the present invention can be prepared according to a different strategy as shown in Scheme 1.

A compound of formula II is alkylated with a reactive intermediate of formula VII wherein $R_3$ is as defined above and X is a leaving group such as a chlorine or a bromine atom or a methane sulphonate, p-toluene sulphonate or a benzene sulphonate group to give a compound of general formula IX wherein $R_1$ and $R_3$ are as defined above. This reaction is preferably carried out in an organic solvent such as toluene, dicloromethane, dioxane or methyl isobutylketone at a temperature between 25° C. and 140° C. in the presence of a base such as an alkali metal carbonate or bicarbonate, triethylamine or diisopropilethylamine.

The alkylation of compound IX with a reactive intermediate of general formula IV wherein $R_2$ is as defined above and X is a leaving group, such as a chlorine or a bromine atom or a methane sulphonate, p-toluensulphonate or a benzenesulphonate group, gives a compound of general formula VIII wherein $R_1$, $R_2$ and $R_3$ are as defined above. This reaction is preferably carried out in an inert solvent such as dimethylformamide, tetrahydrofuran or ethyl ether at a temperature between 0° C. and 80° C. in the presence of an inorganic base such as sodium hydride or sodium amide.

The final products of formula I are purified by chromatography or by recrystallisation. Occasionally, the products are purified by preparative HPLC-MS, using a C-18 column. The starting compounds of formula II are prepared from 4-piperidone following known procedures (*J. Med. Chem.* 1992, 35, 4813).

EXAMPLE 1

Preparation of 5-{4-[1-(2-ethoxyethyl)-1H-indol-3-yl]piperidin-1-ylmethyl}-2-methoxybenzoic acid A. Preparation of 3-(1,2,3,6-tetrahydro-pyridin-4-yl)-1H-indole 30 g (0.26 mol) of indole were dissolved in a solution of potassium hydroxide (77.6 g, 1.38 mol) in methanol (692 ml). 4-piperidone monohydrate hydrochloride (102.3 g, 0.66 mol) was added in one portion and the mixture was heated to reflux for 5 h. Potassium chloride precipitated upon cooling at room temperature and it was filtered off. The liquid phase was concentrated until only one third of the liquid remained in the round-bottom flask. The solid formed during the concentration of the liquid phase was filtered and washed thoroughly with ethanol and, finally, with ethyl ether. 31.9 g (63% of yield) of the final product were obtained.

Melting point: 183-185° C.

B. Preparation of 3-piperidin-4-yl-1H-indole 19.03 g (0.096 mol) of 3-(1,2,3,6-tetrahydro-pyridin-4-yl)-1H-indole were hydrogenated in a Parr apparatus during 18 h at 3 bar with 2.2 g of Pd/C 10% in 600 ml of methanol. After standard work-up, 16.76 g (87% of yield) of the desired product were obtained.

Melting point: 210-212° C.

C. Preparation of 4-(1H-indol-3-yl)-piperidine-1-carboxylic acid ethyl ester

To a suspension of 30 g (0.15 mol) of 3-piperidin-4-yl-1H-indole and 28 mL (0.2 mol) in 185 ml of anhydrous dichloromethane, 17 ml (0.18 mol) of ethyl chloroformate were added dropwise keeping the temperature of the reaction below 20° C. After 2 h at room temperature, the crude mixture was poured into 100 ml of water. The organic layer was separated and dried with sodium sulphate. After filtration, the solvent was removed under reduced pressure affording 39 g (95% of yield) of the expected product.

ESI/MS m/e=272 [(M+1)+, C16H20 N2 O2]
$^1$H—NMR (300 MHz, DMSO) δ=1.16-1.23 (t, 2H), 1.41-1.65 (m, 2H), 1.92-1.99 (m, 2H), 2.90-3.10 (m, 3H), 3.99-4.10 (m, 4H), 6.95-7.10 (m, 3H), 7.31-7.34 (d, 1H), 7.53-7.57 (d, 1H), 10.81 (s, 1H).

D. Preparation of 4-[1-(2-ethoxyethyl)-1H-indol-3-yl]-piperidine-1-carboxylic acid ethyl ester Under inert atmosphere, a solution of 12.5 g (0.045 mol) of 4-(1H-indol-3-yl)-piperidine-1-carboxylic acid ethyl ester in 50 ml of anhydrous DMF was added dropwise to a suspension containing 2.75 g (0.068 mol) of sodium hydride (60% in mineral oil) in 200 ml of anhydrous DMF. After stirring at room temperature for 1 hour, 6.6 ml (0.06 mol) of 1-bromo-2-ethoxyethane were added. The reaction mixture was heated at 60° C. for 3 hours. The crude mixture was poured into water and extracted with ethyl acetate. After drying, the solvent was removed under reduced pressure and 16 g of a crude oil were obtained and used in the next step without purification.

E. Preparation of 1-(2-ethoxyethyl)-3-piperidin-4-yl-1H-indole

To a solution of 16 g (0.054 mol) of 4-[1-(2-ethoxyethyl)-1H-indol-3-yl]-piperidine-1-carboxylic acid ethyl ester in 10 ml of iso-propanol, a solution of 32 g of potassium hydroxide in 270 ml of iso-propanol was added. The crude mixture was refluxed for 16 hours. After cooling at room temperature, the solvent was removed at reduced pressure and the crude mixture was extracted between ethyl acetate and water. The organic layer was dried with sodium sulphate and after filtration, the solvent was removed under reduced pressure affording 9.6 g (71% of yield) of an oil which corresponds to the expected product.

F. Preparation of 5-{4-[1-(2-ethoxyethyl)-1H-indol-3-yl]-piperidin-1-ylmethyl}-2-methoxy-benzoic acid A solution of 1.9 g (0.0071 mol) of 5-bromomethyl-2-methoxy-benzoic acid methyl ester in 5 ml of methyl isobutylketone was added to a suspension of 1.8 g (0.065 mol) of 1-(2-ethoxyethyl)-3-piperidin-4-yl-1H-indole and 1.8 g (0.013 mol) of potassium carbonate in 45 ml of methyl isobutylketone. The reaction mixture was heated at 60° C. for 20 h. The crude mixture was filtered to remove inorganic salts and the solvent was removed under reduced pressure affording 3.5 g of a crude oil. The crude mixture was purified by flash chromatography over silica gel affording 1.8 g (48% of yield) of 5-{4-[1-(2-ethoxyethyl)-1H-indol-3-yl]-piperidin-1-ylmethy}-2-methoxy-benzoic acid ethyl ester. This ester was dissolved in 18 ml of ethanol and hydrolysed with 2N NaOH at room temperature for 20 hours. The crude mixture was neutralised with 2N HCl aqueous solution and the solvent was removed under reduced pressure. The crude residue was extracted between dichloromethane and water. After drying, filtering and removing the solvent under reduced pressure, the residue obtained was recrystallised with ethanol affording 0.77 g (27% of overall yield) of the expected acid.

Melting point: 225.8-226.5° C.

¹H—RMN (DMSO) δ=1.02-1.06 (t, 3H), 1.61-1.72 (m, 2H), 1.90-1.94 (d, 2H), 2.10-2.17 (t, 2H), 2.72-2.79 (t, 1H), 2.89-2.93 (d, 2H), 3.17-3.41 (m, 2H), 3.49 (s, 2H), 3.63-3.69 (t, 2H), 3.81 (s, 3H), 4.22-4.26 (t, 2H), 6.95-6.99 (t, 1H), 7.07-7.12 (m, 3H), 7.40-7.46 (t, 2H), 7.53-7.59 (m, 2H).

EXAMPLE 2

Preparation of 2-methoxy-5-{4-[1-(2-methoxyethyl)-1H-indol-3-yl]piperidin-1-ylmethyl}benzoic acid

A. Preparation of 4-[1-(2-methoxyethyl)-1H-indol-3-yl]-piperidine-1-carboxylic acid ethyl ester This compound was prepared following the procedure described in example 1, part D, starting with 5.5 g (0.02 mol) of 4-(1H-indol-3-yl)-piperidine-carboxylic acid ethyl ester and 2.3 ml (0.0233 mol) of 1-bromo-2-methoxyethane. The reaction mixture was stirred at room temperature for 24 h and after standard work-up, 6.5 g (98% of yield) of 4-[1-(2-methoxyethyl)-1H-indol-3-yl]-piperidine-1-carboxylic acid ethyl ester were obtained.

B. Preparation of 1-(2-methoxyethyl)-3-piperidin-4-yl-1H-indole

This compound was prepared following the procedure described in example 1, part E, starting with 6.5 g (0.02 mmol) of 4-[1-(2-methoxyethyl)-1H-indol-3-yl]-piperidine-1-carboxylic acid ethyl ester. After standard work-up, 4.6 g (92% of yield) of 1-2-methoxyethyl)-3-piperidin-4-yl-1H-indole were obtained.

C. Preparation of 2-methoxy-5-{4-[1-(2-methoxyethyl)-1H-indol-3-yl]piperidin-1-ylmethy}-benzoic acid ethyl ester Over a solution of 6.5 g (0.025 mol) of 1-(2-methoxyethyl)-3-piperidin-4-yl-1H-indole in 90 ml of dichloromethane and 3.9 ml (0.026 mol) of triethylamine, a solution of 7.2 g (0.026 mol) of 5-bromomethyl-2-methoxy-benzoic acid ethyl ester in 15 ml of dichloromethane was added. The crude mixture was stirred at room temperature for 24 hours. After standard work-up and purification by chromatography over silica gel, 9.9 g (70% of yield) of 2-methoxy-5-{4-[1-(2-methoxyethyl)-1H-indol-3-yl]piperidin-1-ylmethy}-benzoic acid ethyl ester were obtained.

D. Preparation of 2-methoxy-5-{4-[1-(2-methoxyethyl)-1H-indol-3-yl]piperidin-1-ylmethyl}-benzoic acid Over a solution of 0.9 g (0.002 mol) of 2-methoxy-5-{4-[1-(2-methoxyethyl)-1H-indol-3-yl]piperidin-1-ylmethy}-benzoic acid ethyl ester in 9 ml of methanol and 5 ml of tetrahydrofuran, 5 ml of a 1N aqueous sodium hydroxide were added. The crude mixture was stirred at room temperature for 20 hours and then neutralised with 1 N aqueous HCl. The product precipitated from the mixture. The solid obtained was filtrated and washed with ethanol and ethyl ether. 0.55 g (65% of yield) of 2-methoxy-5-{4-[1-(2-methoxyethyl)-1H-indol-3-yl]piperidin-1-ylmethyl}-benzoic acid were obtained.

Melting point: 241.9-242.9° C.

¹H—RMN (DMSO) δ=1.59-1.74 (m, 2H), 1.89-1.93 (d, 1H), 2.07-2.15 (t, 2H), 2.71-2.77 (m, 1H), 2.87-2.91 (d, 2H), 3.20 (s, 3H), 3.47 (s, 2H), 3.59-3.63 (t, 2H), 3.79 (s, 3H), 4.22-4.25 (t, 2H), 6.93-6.98 (t, 1H), 7.00-7.10 (m, 3H), 7.39-7.45 (m, 2H), 7.51-7.58 (m, 2H).

EXAMPLE 3

Preparation of 5-[4-(1-butyl-1H-indol-3-yl)-piperidin-1-ylmethyl]-2-methoxybenzoic acid This compound was prepared using the procedure described in Example 1 using 1-bromobuthane instead of 1-bromo-2-ethoxyethane in step D. Step F was performed using 1.3 g (0.0051 mol) of 1-butyl-3-piperidin-4-yl-1H-indole Overall yield 85% (1.4 g).

Melting point: 229.7-235.4° C.

¹H—RMN (DMSO) δ=0.86-0.91 (t, 3H), 1.11-1.30 (m, 4H), 1.68-1.73 (t, 2H), 1.76-2.15 (m, 5H), 2.79-3.16 (m, 2H), 3.74-3.76 (m, 2H), 3.85 (s, 3H), 4.08-4.12 (t, 2H), 6.81-7.19 (m, 4H), 7.38-7.42 (m, 1H), 7.58-7.62 (m, 2H), 7.76-7.80 (m, 1H).

EXAMPLE 4

Preparation of 5-{4-[1-(2-ethoxyethyl)-6-fluoro-1H-indol-3-yl]piperidin-1-ylmethyl}-2-methoxybenzoic acid

A. Preparation of 6-fluoro-3-piperidin-4-yl-1H-indole

This compound was prepared following the procedure described in Example 1 (steps A and B) starting with 1 g (7.4 mmol) of 6-fluoroindol and 2.84 g (18.5 mmol) of 4-piperidone monohydrate hydrochloride. In this case, the hydrogenation step took place for 1 hour at 2 bar and the catalyst used was platinum (IV) oxide. 0.640 g (51% yield) of 6-fluoro-3-piperidin-4-yl-1H-indole were obtained.

ESI/MS m/e=219 [(M+1)+, C13H15 F N2].

B. Preparation of 4-(6-fluoro-1H-indol-3-yl)-piperidine-1-carboxylic acid ethyl ester This compound was prepared following the procedure described in Example 1 (step C) starting with 4.4 g (20 mmol) of 6-fluoro-3-piperidin-4-yl-1H-indole. After standard work-up, 5.2 g (90% of yield) of 4-(6-fluoro-1H-indol-3-yl)-piperidine-1-carboxylic acid ethyl ester were obtained.

C. Preparation of 5-{4-[1-(2-ethoxyethyl)-6-fluoro-1H-indol-3-yl]piperidin-1-ylmethy}-2-methoxybenzoic acid This compound was prepared the procedure described in Example 1 (steps D, E and F) starting with 5.1 g (0.017 mmol) of 4-(6-fluoro-1H-indol-3-yl)-piperidine-1-carboxylic acid ethyl ester. Overall yield 47% (1.4 g)

Melting point: 232.7-233.7° C.

¹H—RMN (DMSO) δ=1.01-1.06 (t, 3H), 1.59-1.67 (m, 2H), 1.89-1.92 (d, 2H), 2.07-2.14 (t, 2H), 2.71-2.75 (m, 1H), 2.87-2.91 (d, 2H), 3.25-3.30 (m, 2H), 3.47 (s, 2H), 3.62-3.65 (t, 2H), 3.80 (s, 3H), 4.19-4.23 (t, 2H), 6.80-6.84 (m, 1H), 7.06-7.12 (m, 2H), 7.27-7.32 (dd, 1H), 7.41-7.45 (d, 1H), 7.50-7.57 (m, 2H).

EXAMPLE 5

Preparation of 5-{4-[6-fluoro-1-(2-methoxyethyl)-1H-indol-3-yl]piperidin-1-ylmethyl}-2-methoxybenzoic acid This compound was prepared following the procedure described in Example 1 (steps D, E and F) starting with 4.4 g (0.015 mmol) of 4-(6-fluoro-1H-indol-3-yl)-piperidine-1-carboxylic acid ethyl ester and 1.7 ml (0.018 mmol) of 1-bromo-2-methoxyethane. Overall yield 30% (0.85 g).

Melting point: 247.0-248.1° C.

$^1$H—RMN (DMSO) δ=1.56-1.75 (m, 2H), 1.87-1.95 (m, 2H), 2.05-2.13 (t, 2H), 2.67-2.71 (t, 1H), 2.86-2.90 (d, 2H), 3.19 (s, 3H), 3.46 (s, 2H), 3.51-3.53 (m, 2H), 3.79 (s, 3H), 4.19-4.23 (m, 2H), 6.78-6.82 (m, 1H), 6.98-7.10 (m, 2H), 7.26-7.30 (dd, 1H), 7.41-7.43 (m, 1H), 7.50-7.55 (m, 2H).

EXAMPLE 6

Preparation of 5-[4-(1-butyl-6-fluoro-1H-indol-3-yl)-piperidin-1-ylmethyl]-2-methoxybenzoic acid

A. Preparation of 5-[4-(6-fluoro-1H-indol-3-yl)-piperidin-1-ylmethyl]-2-methoxybenzoic acid ethyl ester A suspension containing 0.5 g (2.2 mmol) of 6-fluoro-3-piperidin-4-yl-1H-indole, 0.8 g (2.7 mmol) of 5-bromomethyl-2-methoxy-benzoic acid methyl ester and 0.6 g (4.3 mmol) of potassium carbonate in 10 ml of ethyl isobutylketone was heated at 90° C. for 16 hours. The inorganic solid was filtrated and the solvent was removed under reduced pressure. 0.91 g (97% of yield) of the expected product was obtained.

B. Preparation of 5-[4-(1-butyl-6-fluoro-1H-indol-3-yl)-piperidin-1-ylmethyl]-2-methoxybenzoic acid Under inert atmosphere, a solution of 0.07 g (0.17 mmol) of 5-[4-(6-fluoro-1H-indol-3-yl)-piperidin-1-ylmethyl]2-methoxybenzoic acid ethyl ester in 0.5 ml of anhydrous DMF was added dropwise to a suspension containing 0.012 g (0.24 mol) of sodium hydride (60% in mineral oil) in 1 ml of anhydrous DMF. After stirring at room temperature for 1 hour, a solution of 0.044 g (0.24 mol) of 1-bromobuthane in 0.5 ml of DMF was added. The reaction mixture was stirred at room temperature for 15 hours. The solvent was removed under reduced pressure. This ester was dissolved in a mixture of 1 ml of ethanol and hydrolysed with 2N NaOH at room temperature for 20 hours. The crude mixture was neutralised with 2N HCl aqueous solution and the solvent was removed under reduced pressure. The crude residue was purified by HPLC-MS chromatography affording 0.0053 g of the expected acid.

ESI/MS m/e=439 [(M+1)+, C26 H31F N2O3]

Also included within the scope of the present invention are pharmaceutical compositions which comprise, as the active ingredient, at least one indolylpiperidine derivative of general formula I, or a pharmaceutically acceptable salt thereof, in association with a pharmaceutically acceptable carrier or diluent. Preferably the composition is made up in a form suitable for oral, parenteral or topical administration. The pharmaceutically acceptable carriers or diluents which are mixed with the active compound or compounds, or salts thereof, to form the composition of this invention are well-known "per se" and the actual excipients used depend "inter alia" on the intended method of administration of the compositions.

Compositions of this invention are preferably adapted for oral administration. In this case, the compositions may take the form of tablets, capsules or effervescent granules or of liquid preparations such as elixirs, syrups or suspensions, all containing one or more compounds of the invention; such preparations may be made by methods well known in the art. The diluents which may be used in the preparation of the compositions include those liquid and solid diluents which are compatible with the active ingredient, together with colouring or flavouring agents, if desired.

Tablets or capsules may conveniently contain between 0.2 and 500 mg, preferably from 0.5 to 100 mg, of active ingredient or the equivalent amount of a pharmaceutically acceptable salt thereof. The compounds may be incorporated into pellets coated with an appropriate natural or synthetic polymer known in the art to produce sustained release characteristics. They can also be incorporated with polymers into tablet form to produce the same characteristics.

The liquid composition adapted for oral use may be in the form of solution or suspension. The solution may be an aqueous solution of an acid addition salt of the indolylpiperidine derivative in association with, for example, sucrose or sorbitol to form a syrup. The suspension may comprise an insoluble or microencapsulated form of an active compound of the invention in association with water or other pharmaceutically acceptable liquid medium together with a suspending agent or flavouring agent.

Compositions for parenteral injection may be prepared from soluble salts of the indolylpiperidine derivatives, which may or may not be freeze-dried and which may be dissolved in water or an appropriate parenteral injectable fluid. Compositions for topical administration may take the form of a cream, lotion, ointment or the like. They can be prepared as suspensions or emulsions of the type oil-in-water or water-in-oil, using the excipients usual in the art.

In human therapy, the doses of the compound of general formula I depend on the desired effect and duration of treatment; adult doses are generally between 0.2 mg and 500 mg per day and preferably between 0.5 mg and 100 mg per day. In general, the physician will decide the dosing regime taking into account the age and weight of the patient being treated.

Pharmacological Action

The following assays were carried out to demonstrate the excellent pharmacological activities of the compounds of the present invention.

(1) In vitro histamine $H_1$ receptor binding assay, to measure the affinity of the compounds.

(2) Histamine-induced skin vascular permeability in rats, to evaluate antiallergic activity in vivo.

(3) Serotonin 5HT2 receptor binding assay, to assess selectivity.

(1) Histamine-$H_1$ Receptor Binding Assay

The study of binding to histamine-$H_1$ receptors was performed in guinea pig cerebellum membranes as described by Chang et al., *J. Neurochem*, 1979, 32, 1653-1663. Briefly, the membrane suspensions (160 μg/ml) were incubated at 30° C. with 0.7 nM [$^3$H]-mepyramine and different concentrations of the test compounds in a final volume of 250 μl. Binding reactions were terminated by filtration after 30 min of incubation and the bound radioactivity was determined. The non-specific binding was measured in the presence of 10 μM of promethazine. The affinity of each test compound to the receptor was determined by using at least six different concentrations run in duplicate. $IC_{50}$ values were obtained by non-linear regression by use of SAS on a DEC AXP computer.

(2) Histamine-Induced Skin Vascular Permeability in Rats

Male Wistar rats (180-210 g) were treated orally with the test compound or vehicle. Either one, four, eight or 24 hours later the rats were lightly anaesthetised with ether and a cutaneous reaction was induced by two intradermal injections of 50 µl of histamine (100 µg/ml) onto the back, followed by an intravenous injection of 3 ml/kg of Evan's Blue (5 mg/ml), both dissolved in saline. Sixty minutes later, the rats were killed by cervical dislocation and the back skin dissected free. The diameter (in millimetres) of the papule was measured in two directions and the area was calculated. Results are given as the % of inhibition at a given dose compared with the vehicle treated group.

(3) Serotonin-5HT2 Receptor Binding Assay

The study of binding to serotonin-5HT2 receptors was performed in human frontal cerebral cortex membranes as described previously (Pazos et al., Eur. J. of Pharmacol, 1985, 106, 531-538). Briefly, the membrane suspensions (170 µg/ml) were incubated at 37° C. with 1 nM 3H-Ketanserin and different concentrations of the test compounds in a final volume of 250 µl. Binding reactions were terminated by filtration after 30 minutes of incubation under constant shaking and the bound radioactivity was measured. The non-specific binding was estimated in the presence of 10 µM mianserin. The affinity of each test compound to the receptor was determined by using at least six different concentrations run in duplicate. IC50 values were calculated by non-linear regression using SAS.

The indolylpiperidines of the invention are characterised by the presence of a methoxy group in ortho position of the benzoic acid moiety. The results obtained in the pharmacological assays show that this particular structural feature is responsible for an increased antiallergic potency, with respect to indolylpiperidines of otherwise identical structure but not having a methoxy group in ortho position of the benzoic acid moiety, as shown in table 1.

TABLE 1

| Indolylpiperidine core | H1 (nM) | 5HT-2 (nM) | papule (4h) % inh a 1 mg/Kg | H1 (nM) | 5HT-2 (nM) | papule (4h) % inh a 1 mg/Kg | Example |
|---|---|---|---|---|---|---|---|
| 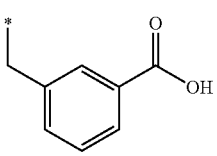 | 218 | 1774 | 84% | 145 | 5350 | 88% | 1 |
| 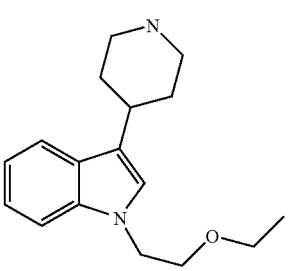 | 335 | >10000 | 24% | 470 | >10000 | 96% | 2 |
| 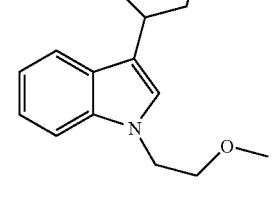 | — | — | — | 130 | 4500 | 100% | 3 |

TABLE 1-continued

| | | | | | | | |
|---|---|---|---|---|---|---|---|
| Indolylpiperidine core | H1 (nM) | 5HT-2 (nM) | papule (4h) % inh a 1 mg/Kg | H1 (nM) | 5HT-2 (nM) | papule (4h) % inh a 1 mg/Kg | Example |
| 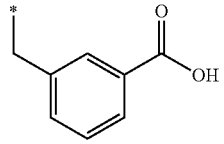 | 147 | 944 | 41% | 160 | 4300 | 89% | 4 |
| 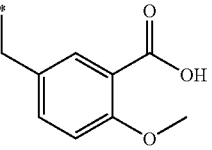 | 150 | 3850 | 44% | 245 | >10000 | 96% | 5 |

The results in table 1 indicate that the compounds of the invention have an H₁ binding IC$_{50}$ which is comparable or even slightly higher than the IC$_{50}$ of the structurally similar indolylpiperidines not having the ortho-methoxy group. These implies a comparable affinity for histamine H₁ receptors in vitro. Consequently, the person skilled in the art would have expected that both classes of indolylpiperidines would also have a comparable antiallergic activity in vivo.

Remarkably, the antihistaminic and antiallergic potency in vivo of the indolylpiperidines of the invention is significantly higher than that of compounds without an ortho-methoxy group. This is evident from the comparison of the inhibitory effects of the two classes of compounds on the size of the papula induced by an injection of histamine, 4 hours after the oral administration of the compounds at a dose of 1 mg/Kg. The percentage of inhibition produced by the compounds of the invention is always higher than that of their counterparts and ranges between 88% and 100%.

Furthermore, the affinity of the compounds of the invention for 5HT-2 receptors is in all cases significantly lower than the already relatively low affinity of the compounds not having an ortho-methoxy group. The affinity for 5HT-2 receptors is known to be directly correlated with the occurrence of the serious cardiovascular side-effects which many commercial antihistamines induce. Therefore, it is highly desirable to develop compounds with increased 5HT-2 binding IC$_{50}$, because this results in a more selective antihistaminic effect. This is the case of the indolylpiperidines of the invention, which are expected to be devoid of cardiovascular effects.

In view of these results it can be concluded that the distinguishing structural features of the compounds of the invention represent a novel group of compounds selected from the generic class of antihistaminic indolylpiperidines, which results in a dramatic improvement of their selectivity and antiallergic potency and in a decreased risk of producing cardiovascular side-effects.

They can thus be advantageously used at low doses for the treatment of allergic disorders, for instance, bronchial asthma, rhinitis, conjunctivitis, dermatitis and urticaria.

The invention thus provides a method for treating an allergic disorder comprising the step of administering to a subject in need of such treatment an effective amount of a compound of formula I.

The invention also provides the use of the compounds of formula I in the manufacture of a medicament for the treatment of an allergic disorder, as well as pharmaceutical compositions comprising a compound of formula I. Some examples of suitable compositions are shown below.

FORMULATION EXAMPLE 1

Preparation of a pharmaceutical composition: syrup
150 ml of a syrup are prepared as follows:

| | |
|---|---|
| Active compound | 750 mg |
| Glycerin | 15 g |
| hydrogenated castor oil-ethylene oxide | 1.5 g |
| sodium methyl p-hydroxybenzoate | 240 mg |
| sodium propyl p-hydroxybenzoate | 60 mg |
| sodium saccharin | 300 mg |
| flavouring q.s. | |
| sodium hydroxide q.s. pH = 4 | |
| demineralised water q.s. 150 ml | |

Procedure:

To a solution of the p-hydroxybenzoates and saccharin in 30 ml of demineralised water, an aqueous glycerin solution and hydrogenated castor oil-ethylene oxide are added. After stirring, the active compound is added and homogenised to reach complete dissolution. The flavouring agent is then mixed into the solution with vigorous stirring, and the mixture was made up to final volume with demineralised water.

FORMULATION EXAMPLE 2

Preparation of a Pharmaceutical Composition: Capsules

Capsules containing 20 mg of active compound are prepared from the following formulation:

| | |
|---|---|
| Active compound | 20 mg |
| magnesium stearate | 4.5 mg |
| lactose spray dried | 367 mg |
| cross-linked sodium carboxymethylcellulose | 18 mg |
| sodium lauryl sulphate | 9 mg |

Procedure:

2-methoxy-5-{4-[1-(2-methoxy-ethyl)-1H-pyrrolo[2,3-b]pyridin-3-yl]-piperidin-1-ylmethyl}-benzoic acid, sodium lauryl sulphate, lactose and cross-linked sodium carboxymethylcellulose were mixed together and passed through a screen with an opening of 0.6 mm. The magnesium stearate was added and the mixture encapsulated into gelatine capsules of appropriate size.

FORMULATION EXAMPLE 3

Preparation of a Pharmaceutical Composition: Tablets

Tablets containing 10 mg of active compound were prepared from the following formulation:

| | |
|---|---|
| Active compound | 10 mg |
| microcrystalline cellulose | 16.5 mg |
| lactose spray dried | 96.2 mg |
| carboxymethyl starch | 5.7 mg |
| sodium stearyl fumarate | 0.8 mg |
| colloidal silicon dioxide | 0.8 mg |

Procedure:

All the powders were passed through a screen with openings of 0.6 mm. They were then all mixed for 30 minutes and compressed into 145 mg tablets using 6 mm discs and flat bevelled punches. The disintegration time of the tablets was about 60 seconds.

FORMULATION EXAMPLE 4

Preparation of a Cream

Components:

| | |
|---|---|
| Active compound | 1% |
| Cetyl alcohol | 3% |
| Stearyl alcohol | 4% |
| Gliceryl monostearate | 4% |
| Sorbitan monostearate | 0.8% |

-continued

| | |
|---|---|
| Sorbitan monostearate POE | 0.8% |
| Liquid vaseline | 5% |
| Methylparaben | 0.18% |
| Propylparaben | 0.02% |
| Glycerine | 15% |
| Purified water csp. | 100% |

An oil-in-water emulsion cream is prepared with the ingredients listed above, using conventional methods.

The invention claimed is:

1. A compound of formula I

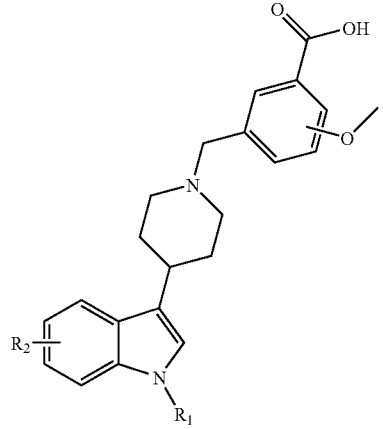

(I)

wherein:

$R_1$ represents an alkyl, alkenyl, alkoxyalkyl or cycloalkylalkyl group;

$R_2$ represents a hydrogen or halogen atom; and wherein the methoxy group substituting the benzoic acid is in position ortho with respect to the carboxy groups and in position para with respect to the carbon atom that is bound to the indolylpiperidine moiety;

or a pharmaceutically acceptable salt thereof.

2. A compound according to claim 1, wherein $R_1$ is chosen from ethyl, n-propyl, n-butyl, methoxymethyl, methoxyethyl, ethoxyethyl, cyclopropylmethyl, cyclopentylmethyl, cyclohexylmethyl, cyclopropylethyl, allyl, 2-propenyl, 2-propoxyethyl and 3-methoxypropyl.

3. A compound according to claim 2, wherein $R_1$ is methoxyethyl, ethoxyethyl, butyl, cyclopropylmethyl or allyl.

4. A compound according to claim 1, wherein $R_2$ is hydrogen, fluorine or chlorine.

5. A compound according to claim 4, wherein $R_2$ is hydrogen, fluorine or chlorine.

6. A compound according to claim 1, chosen from:

5-{4-[1-(2-ethoxyethyl)-1H-indol-3-yl]piperidin-1-ylmethyl}-2-methoxybenzoic acid;

2-methoxy-5-{4-[1-(2-methoxyethyl)-1H-indol-3-yl]piperidin-1-ylmethyl}-benzoic acid;

5-[4-(1-butyl-1H-indol-3-yl)-piperidin-1-ylmethyl]-2-methoxybenzoic acid;

5-{4-[1-(2-ethoxyethyl)-6-fluoro-1H-indol-3-yl]piperidin-1-ylmethyl}-2-methoxybenzoic acid;

5-{4-[6-fluoro-1-(2-methoxyethyl)-1H-indol-3-yl]piperidin-1-ylmethyl}-2-methoxybenzoic acid;

5-[4-(1-butyl-6-fluoro-1H-indol-3-yl)-piperidin-1-ylmethyl]-2-methoxybenzoic acid;

5-[4-(5-bromo-1-propyl-1H-indol-3-yl)-piperidin-1-ylmethyl]-2-methoxybenzoic acid;

3-[4-(5-chloro-1-ethyl-1H-indol-3-yl)-piperidin-1-ylmethyl]-2-methoxybenzoic acid;

3-[4-(1-cyclopropylmethyl-5-fluoro-1H-indol-3-yl)-piperidin-1-ylmethyl]-2-methoxybenzoic acid;

5-[4-(5-chloro-1-cyclohexylmethyl-1H-indol-3-yl)-piperidin-1-ylmethyl]-2-methoxybenzoic acid;

2-methoxy-5-{4-[1-(2-propoxyethyl)-1H-indol-3-yl]-piperidin-1-ylmethyl}-benzoic acid;

3-{4-[5-bromo-1-(3-methoxypropyl)-1H-indol-3-yl]-piperidin-1-ylmethyl}-2-methoxybenzoic acid;

3-[4-(1-allyl-1H-indol-3-yl)-piperidin-1-ylmethyl]-2-methoxybenzoic acid;

3-[4-(1-allyl-6-fluoro-1H-indol-3-yl)-piperidin-1-ylmethyl]-2-methoxybenzoic acid;

5-{4-[5-chloro-1-(2-propenyl)-1H-indol-3-yl]-piperidin-1-ylmethyl}-2-methoxybenzoic acid;

5-[4-(1-cyclopentylmethyl-6-fluoro-1H-indol-3-yl)-piperidin-1-ylmethyl]-2-methoxybenzoic acid;

3-{4-[6-fluoro-1-methoxymethyl-1H-indol-3-yl]-piperidin-1-ylmethyl}-2-methoxybenzoic acid;

3-{4-[1-cyclopropylethyl-1H-indol-3-yl]-piperidin-1-ylmethyl}-2-methoxybenzoic acid;

3-{4-[5-chloro-1-(2-methoxyethyl)-1H-indol-3-yl]-piperidin-1-ylmethyl}-2-methoxybenzoic acid; and 3-{4-[1-(2-ethoxyethyl)-5-fluoro-1H-indol-3-yl]-piperidin-1-ylmethyl}-2-methoxybenzoic acid.

7. A compound according to claim 6, chosen from:

5-{4-[1-(2-ethoxyethyl)-1H-indol-3-yl]piperidin-1-ylmethyl}-2-methoxybenzoic acid;

2-methoxy-5-{4-[1-(2-methoxyethyl)-1H-indol-3-yl]piperidin-1-ylmethyl}-benzoic acid;

5-[4-(1-butyl-1H-indol-3-yl)-piperidin-1-ylmethyl]-2-methoxybenzoic acid;

5-{4-[1-(2-ethoxyethyl)-6-fluoro-1H-indol-3-yl]piperidin-1-ylmethyl}-2-methoxybenzoic acid;

5-{4-[6-fluoro-1-(2-methoxyethyl)-1H-indol-3-yl]piperidin-1-ylmethyl}-2-methoxybenzoic acid; and 5-[4-(1-butyl-6-fluoro-1H-indol-3-yl)-piperidin-1-ylmethyl]-2-methoxybenzoic acid.

8. A pharmaceutical composition comprising an effective amount of at least one compound as defined in claim 1, and at least one pharmaceutically acceptable diluent or carrier.

9. A method for treating a subject afflicted with a pathological condition or disease is chosen from bronchial asthma, allergic rhinitis, conjunctivitis, dermatitis, and urticaria comprising administering to said subject an effective amount of at least one compound as defined in claim 1.

* * * * *

UNITED STATES PATENT AND TRADEMARK OFFICE
CERTIFICATE OF CORRECTION

PATENT NO.       : 7,560,471 B2                                            Page 1 of 1
APPLICATION NO. : 10/515407
DATED            : July 14, 2009
INVENTOR(S)      : Fonquerna Pou et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1037 days.

Signed and Sealed this

Seventh Day of September, 2010

David J. Kappos
*Director of the United States Patent and Trademark Office*